United States Patent [19]

Kotuby

[11] 4,158,361

[45] Jun. 19, 1979

[54] DISPENSING SYSTEM FOR DIRECTING LIQUID TO A DEFINED AREA

[75] Inventor: Paul M. Kotuby, Naugatuck, Conn.

[73] Assignee: The Risdon Manufacturing Company, Naugatuck, Conn.

[21] Appl. No.: 837,813

[22] Filed: Sep. 29, 1977

[51] Int. Cl.$^2$ .............................................. A61M 11/00
[52] U.S. Cl. ................................. 128/173 R; 222/182; 222/402.13
[58] Field of Search ................... 128/203, 208, 173 R, 128/248, 249; 239/288.5; 222/182, 183, 402.1, 402.12, 402.13, 562

[56] References Cited

U.S. PATENT DOCUMENTS

| 1,853,242 | 4/1932 | Sliter | 128/173 R |
| 2,707,968 | 5/1955 | Efford | 222/182 |
| 3,012,555 | 12/1961 | Meshberg | 222/402.13 |
| 3,698,604 | 10/1972 | Nigro | 222/182 |
| 3,768,475 | 10/1970 | Osborne | 222/402.11 |

Primary Examiner—Robert J. Spar
Assistant Examiner—H. Grant Skaggs

Attorney, Agent, or Firm—St. Onge, Steward, Johnston, Reens & Noë

[57] ABSTRACT

A dispensing system is disclosed for use with a liquid dispensing package that includes a container and a system for forcing liquid from the container. The dispensing system directs liquid forced from the container to a defined area such as the eye and comprises a selectively operable nozzle that is mounted with the container to be movable relative thereto between liquid-dispensing and closed positions. The nozzle has an outlet orifice from which liquid is dispensed. An overcap is mounted in fixed relation with the container and defines an opening with which the nozzle orifice is registered when in the liquid-dispensing position. A shield, which directs liquid from the nozzle to the defined area, has an inlet aperture, a coupling arrangement for mounting the shield on the overcap with the inlet aperture registered with the overcap opening, and an outlet aperture remote from the inlet aperture. The construction of the nozzle, overcap and shield and the arrangement for mounting them on the container permits the nozzle to be moved, relative to the container, without moving the shield.

5 Claims, 4 Drawing Figures

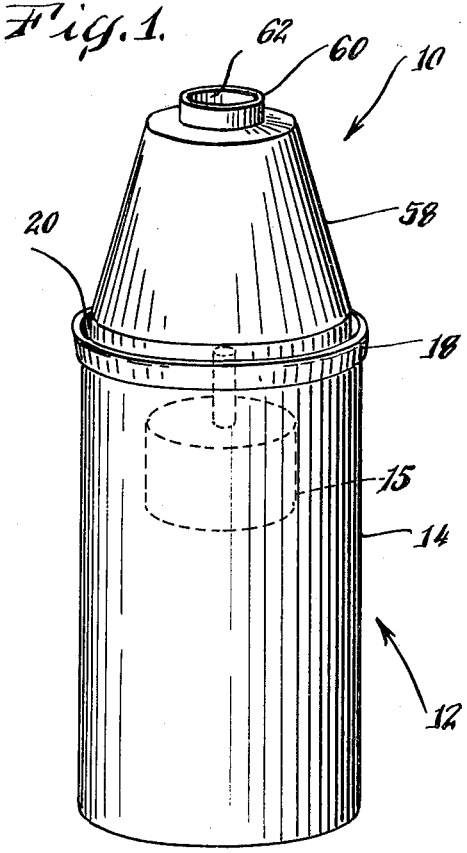
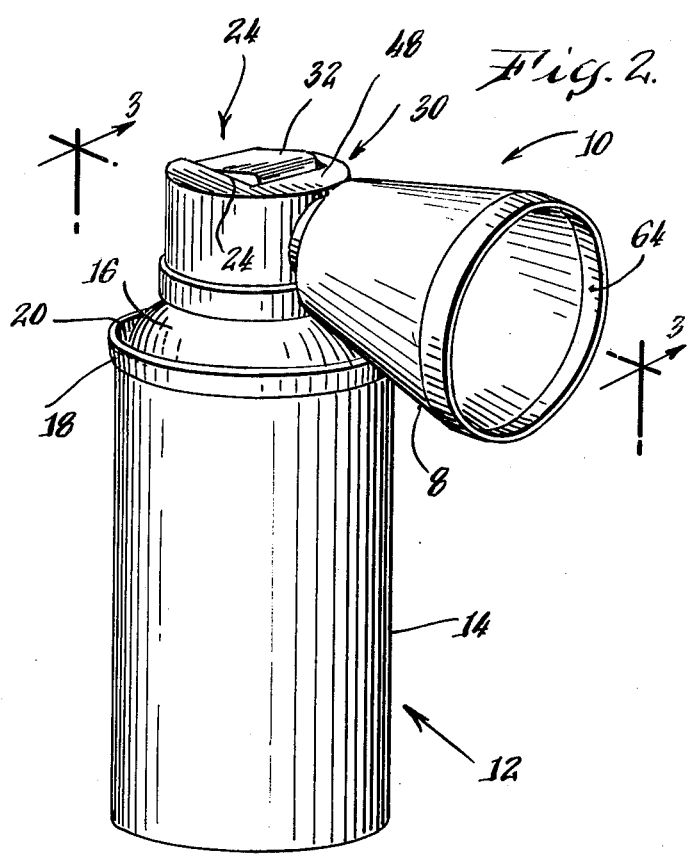
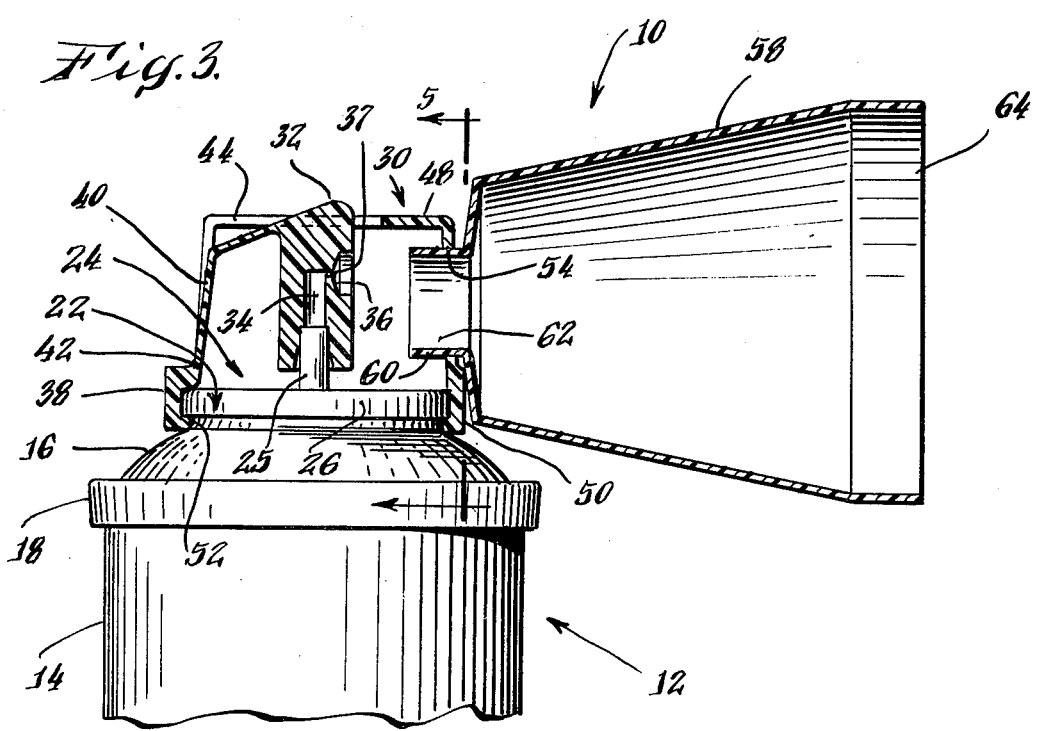

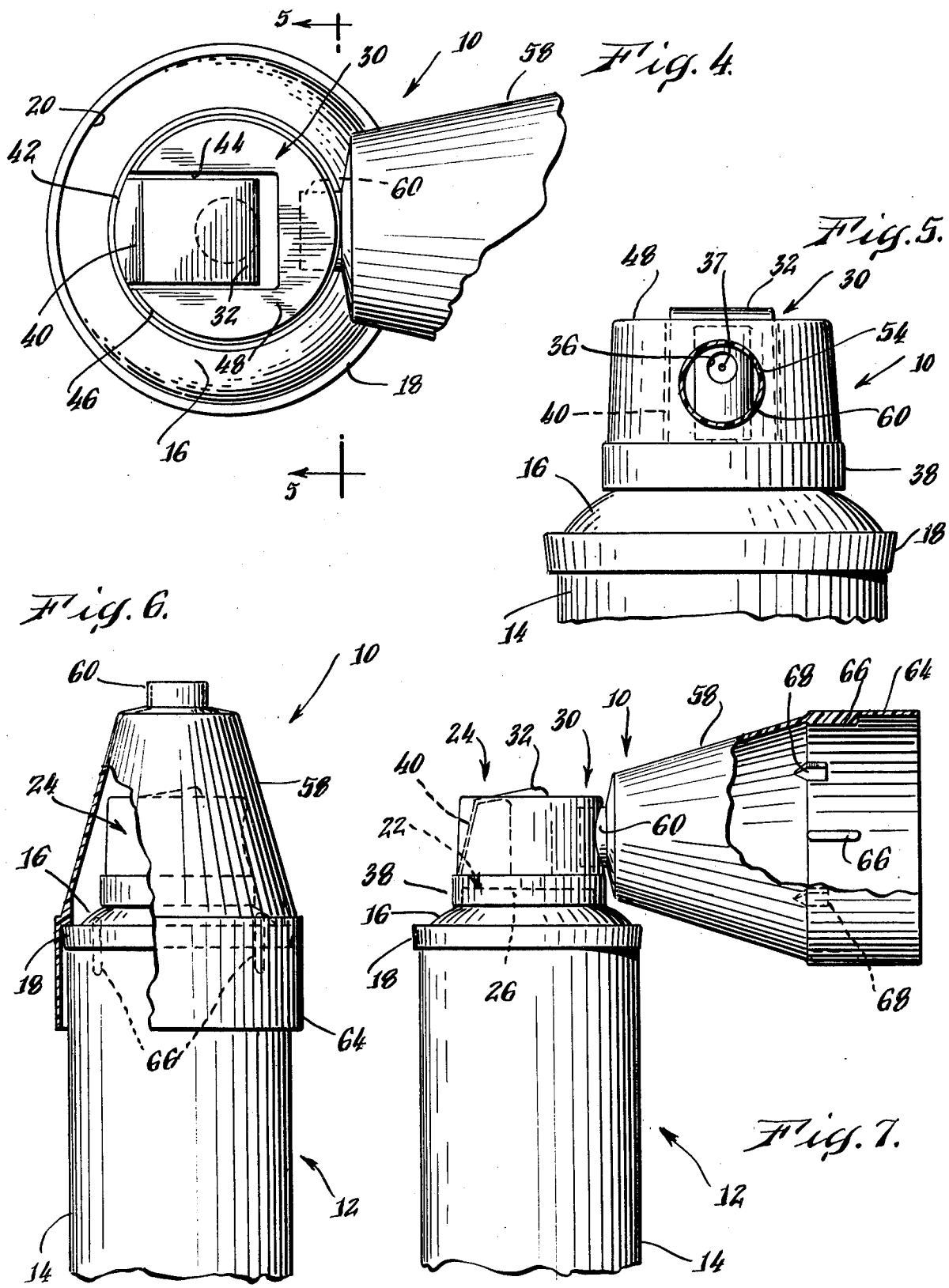

DISPENSING SYSTEM FOR DIRECTING LIQUID TO A DEFINED AREA

BACKGROUND OF THE INVENTION

1. Field of the Invention

The present invention relates to a dispensing system for directing a liquid forced from a container to a defined area.

There are many applications in which liquid dispensed from a container in atomized fashion, that is as a spray, should be confined to reach a specific, well-defined area. For example, pharmaceutical products for relieving irritation of the eye should be dispensed directly to the eye without reaching large portions of the surrounding facial area. Products for the eye, in the past have been most frequently dispensed with a dropper in drop-by-drop fashion. However, this technique has certain disadvantages. In particular, it is messy and often wasteful. Further, it requires that the treated person lie down or otherwise tilt his head back to receive the product drop.

Aerosol and pump systems for dispensing such products have also been proposed. These systems have the advantage of not requiring that the treated person's head be tilted. Further, waste is minimized. However, such systems suffer from certain other drawbacks.

For purposes of this specification and the concluding claims, the term "liquid" is intended to mean a liquid, powder, liquid-powder composition or any other similar composition which may be desirably dispensed from an aerosol or pump-type package.

2. Description of the Prior Art

Typical aerosol and pump spray systems for dispensing liquid such as eye treatment products are disclosed in U.S. Pat. Nos. 3,841,533 (Carroll et al.); 3,314,426 (Carroll); 3,012,555 (Meshberg); Re. 26,304 (Meshberg); 2,985,382 (Coplan); and 2,890,697 (Van Sickle). Each of these patents discloses a device in which a shield, generally conical in shape, is attached to the spray nozzle of a pump bottle or an aerosol container. In the device disclosed in the Carroll et al. Patent, for example, the shield may be mounted to enclose the spray nozzle during periods of non-use and may be mounted on the spray nozzle to direct spray therefrom to a specific area when the package is in use. The nozzle and shield are formed in such a way that liquid can be dispensed through the nozzle orifice and the shield when in operative relation. However, when the shield covers the nozzle for storage, the nozzle orifice is closed from exposure to the environment.

The Coplan and Meshberg Patents disclose shields which are also mountable on the container to protect the nozzle. However, in each of the patents noted above as in the Carroll et al. device, the shield is mounted in an operable position directly on the spray nozzle. Accordingly, the shield and the nozzle are simultaneously depressed to dispense contents of the container. This arrangement creates problems, especially when the apparatus is being used to apply pharmaceutical products to the eye. In particular, it is difficult to manipulate both the nozzle and the container when one is moved relative to the other. That is, assuming the shield is placed against the eye, the container must be moved up toward it to dispense product if the shield is not to move relative to the eye. Alternatively, the shield may be depressed down toward the container but such movement would shift it from its proper position adjacent the eye.

The apparatus of the present invention is intended to solve the problem noted above.

SUMMARY OF THE INVENTION

In a preferred embodiment to be described below in detail, the liquid dispensing system of the present invention permits application of a liquid to a defined area without undesirable agitation caused by movement of various components of the dispensing package relative to other of its components. Moreover, this dispensing system is adaptable with equal advantage to aerosol liquid dispensing packages and pump-type liquid dispensing packages.

In its preferred embodiment, the system of the present invention is designed for use with a dispensing package that includes a container and means for forcing liquid from the container. Typically, such means will either be a pump such as that disclosed in U.S. Pat. No. 4,056,216 (Kotuby) filed Apr. 13, 1976, or an aerosol arrangement for dispensing the contents of the container under pressure. The package is oridinarily operated by depressing a pump actuator toward the container. In an aerosol system, the package is operated by depressing a valve actuator toward the container. Thus, in both cases, the motion necessary to operate the package is the same.

The liquid dispensing system of the invention, for use with either type liquid dispensing package, directs liquid forced from the container to a defined area and comprises a selectively operable nozzle which is mounted with the container and movable thereto between liquid-dispensing and closed positions. This nozzle, in the case of a pump-type package, is mounted atop the pump actuator; in the case of an aerosol package, is mounted atop the aerosol valve actuator. The nozzle has an outlet orifice from which liquid is dispensed when forced from the container by either the pump or aerosol system.

The system of the invention further comprises an over-cap which is mounted in fixed relation with the container and defines an opening with which the nozzle orifice is registered when in liquid-dispensing position. A shield for directing liquid from the nozzle to the defined area has an inlet aperture, a coupling for mounting the shield on the overcap with the inlet aperture registered with the overcap opening, and an outlet aperture remote from the inlet aperture.

Since the shield is mounted in operable position with the overcap, it is also mounted in fixed relation to the container. Further, the nozzle, when moved to its liquid-dispensing system, moves relative to both the container and the shield. Therefore, an applicator merely holds the container with the shield in position to dispense liquid toward the desired area, while actuating the nozzle. Such actuation does not disturb the position of the shield relative to the container, and, accordingly, the liquid may be dispensed with certainty toward that area.

The overcap and nozzle are also constructed in such a fashion that the outlet orifice of the nozzle is always registered with the opening in the overcap. Further, the shield is designed to serve as a protective cover for the end of the container equipped with the nozzle and overcap during periods of non-use. Therefore, the nozzle orifice is protected against contamination during such times.

The shield and overcap do not have special alignment features. However, because of their design, they can only be operably assembled in one attitude.

Accordingly, it is an object of the present invention to provide a dispensing system for directing liquid from a package to a confined area, such as the eye, in a manner which avoids unnecessary agitation of the package during dispensing.

Other objects, aspects and advantages of the present invention will be pointed out in or will be understood from the following detailed description provided below in conjunction with the accompanying drawings.

BRIEF DESCRIPTION OF THE DRAWINGS

FIG. 1 is a perspective view of the liquid dispensing system of the present invention and a package in conjunction with which it is used, shown with the liquid shield attached as a protective cover.

FIG. 2 is a perspective view of the system and package, similar to that shown in FIG. 1, with the shield mounted with the overcap for operation.

FIG. 3 is a vertical cross-sectional view taken through Plane 3—3 in FIG. 2 illustrating internal details of the liquid dispensing system.

FIG. 4 is a top plan view of the system.

FIG. 5 is a front elevational view, taken partly in cross-section from plane 5—5 in FIG. 4, of the liquid dispensing system and the overcap with the shield removed therefrom.

FIG. 6 is a side elevational view of a second embodiment of the dispensing system of the present invention.

FIG. 7 is a side elevational view, partly broken away to show detail, of the second embodiment.

DETAILED DESCRIPTION OF THE PREFERRED EMBODIMENTS

As shown in FIG. 1, the liquid dispensing system of the present invention, generally indicated at 10, forms a part of a liquid dispensing package, generally indicated at 12, that includes a container 14. The package may comprise a pressurized aerosol container of conventional design that holds a liquid product which is either missible or immissible with a propellant having a liquid phase and a gaseous phase confined as a pressure head above the product and liquid propellant phase. Alternatively, the package may include a non-pressurized container equipped with a pump for dispensing liquid therefrom. Such a system 15 for forcing liquid from the container is shown diagrammatically in FIG. 1. For convenience, the present invention will be described with reference to an aerosol package.

Container 14 is equipped at its top with an end piece 16 secured to the container by any suitable means, such as a conventional crimp seal 18 which forms a depressed annular channel or retaining lip 20 encircling the margin of the end piece 16. An aperture 22 is formed in the center of the end piece to receive a valve cup 24 which is equipped with a conventional aerosol valve (not shown) which is then mounted inside the container. The valve cup is secured to the aperture of the end piece by any conventional means such as a crimp seal to form an annular ferrule 26.

As shown in FIG. 3, a stem 25 projects upwardly from the valve cup and is the actuator for the aerosol valve. That is, the stem may be depressed inwardly of the container or tilted, to dispense liquid therefrom.

That portion of the liquid dispensing package described above is conventional. The liquid dispensing system of the present invention cooperates with this conventional package to achieve the objectives of the present invention.

The liquid dispensing system of the invention comprises an integrally formed nozzle and overcap assembly generally indicated at 30. This assembly comprises a nozzle member 32 formed with a cylindrical, axially extending socket 34 which is dimensioned to receive the valve stem 25 with a press fit. Extending radially from the socket is a turbulence inducing formation 36, which may be in the form of a one or two piece mechanical breakup assembly, for atomizing liquid which passes therethrough. The formation terminates in an outlet orifice 37. Accordingly, the aerosol valve may be actuated by depressing the nozzle 32 to in turn depress the valve stem inwardly of the container. When the valve is so actuated, the pressure in the container forces liquid through the valve, the valve stem, the nozzle, and out of the outlet orifice to be dispensed.

As can be seen in FIG. 3, the nozzle 32 is integrally formed with an overcap 38 through a thin flexible web 40. The web is joined to the overcap at a flexible hinge 42. Further, as can be seen in FIGS. 3 and 4, the web and nozzle are separated from the remainder of the overcap 38 by C-shaped slot 44. Accordingly, the nozzle may be depressed relative to the overcap through flexing of the hinge 42 and the web 40.

The remainder of the overcap assembly comprises a generally cylindrical enclosure 46 that is sealed at the top by a cover plate 48 which extends to the margin of the slot 44 to rim the web 40 of the nozzle 32. The overcap terminates at its lower margin in a cylindrical skirt 50 which is formed with an annular rib 52 on its inner surface. This annular rib is designed to clamp under the ferrule 26 formed at the attachment of the valve cup with the container end piece to hold the nozzle-overcap assembly in tight interengagement with the container and to hold nozzle socket 34 in engagement with the valve stem 26.

The overcap 38 is also formed with an enlarged opening 54 in its front face as can be seen in FIGS. 3 and 5. The outlet orifice 37 of the turbulence inducing portion 36 of the nozzle 32 is registered with the opening 54 at all times as can been seen in FIG. 5. That is, in both the closed position of the nozzle and in the depressed, liquid-dispensing position of the nozzle, the outlet orifice 56 and opening 54 are aligned so that liquid may be dispensed freely from the overcap assembly 30. Further, by virtue of the integral formation of the overcap and nozzle, rotation of the assembly relative to the container does not disturb the registry of the nozzle orifice and the over-cap opening.

The liquid dispensing system of the invention further comprises a structure for directing spray from the nozzle orifice to a well defined area, such as the eye. In the first embodiment, this structure is illustrated in the form of a frustoconical or bell-shaped shield 58 having a cylindrical boss 60 at its smaller end. The boss is dimensioned to be press fitted into the overcap opening 54, as shown in FIGS. 2 and 3 thereby establishing a coupling between the shield and overcap. The shield 58 is further formed with an inlet aperture 62 which extends through the boss 60 and is accordingly registered with the nozzle orifice when the shield is operably attached to the overcap. The shield also has an outlet aperture 64 at its enlarged end that is remote from the inlet aperture. Accordingly, it can be seen from FIG. 3 that the shield functions to continue spray from the nozzle orifice to its outlet aperture.

In order to use the liquid dispensing system of the invention, for example, to apply a medication to the eye, the shield is assembled in operative condition with its boss inserted into the opening in the overcap as shown in FIGS. 2 through 5. The outlet aperture of the shield is then placed over the eye. The nozzle is depressed to actuate the aerosol valve and dispense the liquid through the nozzle orifice. The dispensed liquid is confined by the shield to reach only the eye provided that the outlet aperture end is pressed tightly against the immediately surrounding facial area.

The actuation of the nozzle does not disturb the position of the shield. That is, the overcap is mounted in fixed relation to the container and the shield is mounted in fixed relation to the overcap. Actuation of the nozzle does not disturb the relationship between these three components. Therefore, an operator holding the container with the shield in position to dispense liquid can actuate the nozzle without moving the shield relative to the container. This arrangement provides substantial advantages over prior art structures in that unwanted agitation of the shield is avoided. Liquid may be dispensed toward the desired area with certainty. The advantages noted above are even more pronounced in pump-type packages where greater package agitation oridinarily results from depression of the pump plunger. However, when the dispensing system of the present invention is employed, depression of a pump plunger does not disturb the position of the shield relative to the container and overcap.

As can be seen in FIG. 2, the exterior of the outlet aperture of the shield is adapted to be snap-fitted into the annular channel defined at the valved end of the container. In this fashion, the overcap and nozzle are completely enclosed, except for the relatively small inlet aperture 60 to the shield.

FIGS. 6 and 7 illustrate an alternative embodiment in which the shield is formed with an enlarged cylindrical skirt 64 at the end of its outlet aperture. This skirt is dimensioned to embrace the outer portion of the connection between the container end piece 16 and the container 14 of the liquid dispensing package. Further, the interior of skirt 64 is formed with axially extending ribs 66 that grip the end piece-container crimp seal to hold the shield thereon. Shorter, enlarged ribs 68, properly position the shield on the container as shown in FIG. 6.

Thus, both embodiments of the present invention provide a valuable protection for the nozzle and overcap when the package is stored. Moreover, this protection is a substantial improvement over prior art designs in that the inlet aperture to the shield is axially disposed thereon. Therefore, it forms the only opening to the nozzle and overcap when installed in the closed position, and it is remote from the nozzle orifice. This configuration represents a substantial improvement over prior art apparatus in which the shield is attached through a radially disposed opening to the nozzle.

It can further be seen from the above description that the liquid dispensing system of the present invention provides substantial improvements over prior art systems. It permits positive dispensing of liquid in spray form to a wall defined area and further confines spray to that area.

Accordingly, although specific embodiments of the present invention have been described above in detail, it is to be understood that this is for purposes of illustration. Modifications may be made to the liquid dispensing system structures by those skilled in the art in order to adapt them to particular applications.

What is claimed is:

1. In a liquid dispensing package including a container and means for forcing the liquid from the container, a dispensing system for directing liquid forced from the container to a defined area such as the eye and comprising:

A. a nozzle, operatively connected to said means for forcing liquid from said container, movable between a liquid dispensing position depressed toward said container and a closed position returned away therefrom, and having an outlet orifice for dispensing liquid therethrough when said nozzle is depressed to said liquid dispensing position;

B. an overcap, mounted with said container in a fixed axial position relative thereto, defining an opening registerable with said outlet orifice when said nozzle is moved to said liquid-dispensing position; and C. a shield both mountable with said container to enclose and protect said nozzle and said overcap when said package is not in use and mountable with said overcap to direct liquid dispensed through said outlet orifice of said nozzle and said overcap opening to said defined area when said nozzle is depressed to said liquid dispensing position, said shield comprising a generally frustoconical member having a tubular boss, defining an inlet aperture, shaped and sized to be removably press fitted into said overcap opening, said shield thereby being mountable in a fixed position relative to said overcap and thus said container, and said member further defining an outlet aperture, relatively larger than said inlet aperture, shaped and sized to engage said defined area when said shield is mounted with said overcap as aforesaid and to engage the container in the region of said nozzle and overcap thereby being mountable with said container to protect said nozzle and overcap as aforesaid, whereby said nozzle may be depressed to said liquid dispensing position when said shield is mounted with said overcap without disturbing the fixed positional relationship between said shield, said overcap and said container.

2. The dispensing system for use in a liquid dispensing package as claimed in claim 1 further comprising:

flexible hinge means for interconnecting said nozzle and said overcap and for permitting relative movement therebetween.

3. The dispensing system for use in a liquid dispensing package as claimed in claim 2 wherein said nozzle and overcap are integrally formed together with said flexible hinge means.

4. The dispensing system for use in a liquid dispensing package as claimed in claim 1 wherein said shield outlet aperture is shaped to embrace the end of the container on which said nozzle is mounted.

5. The dispensing system for use in a liquid dispensing package as claimed in claim 1 wherein the said container is formed with a retaining lip and wherein the margin of said shield outlet aperture is shaped to be engaged with the container retaining lip.

* * * * *